United States Patent [19]

Priegnitz et al.

[11] 4,270,013
[45] May 26, 1981

[54] PROCESS FOR THE SEPARATION OF NITROTOLUENE ISOMERS

[75] Inventors: James W. Priegnitz, Elgin; Arthur M. Landis, Carpentersville, both of Ill.

[73] Assignee: UOP Inc., Des Plaines, Ill.

[21] Appl. No.: 86,489

[22] Filed: Oct. 19, 1979

[51] Int. Cl.³ .............................................. C07C 79/10
[52] U.S. Cl. .................................................... 568/940
[58] Field of Search ................. 568/924, 927, 939, 940

[56] References Cited

U.S. PATENT DOCUMENTS

| | | | |
|---|---|---|---|
| 1,836,212 | 12/1931 | Weiland et al. | 568/940 |
| 3,030,415 | 4/1962 | Fields | 568/940 X |
| 3,232,999 | 2/1966 | Brogden et al. | 568/940 X |

*Primary Examiner*—Leland A. Sebastian

*Attorney, Agent, or Firm*—James R. Hoatson, Jr.; Louis A. Morris; William H. Page, II

[57] ABSTRACT

An adsorptive separation process for separating ortho or para-nitrotoluene from a feed mixture comprising the isomer to be separated and at least one other isomer of nitrotoluene, or for separating ortho and para-nitrotoluene from a mixture of all three isomers of nitrotoluene, which process comprises contacting the feed mixture with an adsorbent comprising a type X or type Y zeolite, whichever is appropriate, containing at the exchangeable cationic sites the appropriate cations, selectively adsorbing substantially all of the nitrotoluene to be separated to the substantial exclusion of the remaining isomers and thereafter recovering high-purity ortho, para or ortho and para isomers. A desorption step may be used to desorb the adsorbed isomers.

20 Claims, No Drawings

PROCESS FOR THE SEPARATION OF NITROTOLUENE ISOMERS

BACKGROUND OF THE INVENTION

1. Field of the Invention

The field of art to which the claimed invention pertains is solid-bed adsorptive separation. More specifically, the claimed invention relates to a process for the separation of isomers of nitrotoluene from a feed mixture comprising such isomers which process employs a solid adsorbent which selectively removes the selected isomers from the feed mixture thereby producing a fluid raffinate stream comprising a mixture of the non-adsorbed isomers.

2. Description of the Prior Art

The nitrotoluenes are important starting materials for the manufacture of dyes and explosives.

It is well known in the separation art that certain crystalline aluminosilicates can be used to separate hydrocarbon species from mixtures thereof. The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423 for example disclose processes in which large pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyltrisubstituted benzene; and in U.S. Pat. No. 3,668,267 a particular zeolite is used to separate specific alkyl-substituted naphthalenes. In processes described in U.S. Pat. Nos. 3,558,732; 3,686,342 and 3,997,620, adsorbents comprising particular zeolites are used to separate para-xylene from feed mixtures comprising para-xylene and at least one other xylene isomer by selectively adsorbing para-xylene over the other xylene isomers. In the last mentioned processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. Also, in the last mentioned processes the adsorption and desorption may be continuously in a simulated moving bed countercurrent flow system, the operating principles and sequence of which are described in U.S. Pat. No. 2,985,589.

We have discovered a method of using zeolites for the separation of nitrotoluene isomers, particularly the ortho and/or para isomers from a mixture of the isomers. Our invention comprises the use of specific zeolites, which we have found to exhibit selectivity for the ortho and/or para isomers of nitrotoluene.

SUMMARY OF THE INVENTION

It is accordingly a broad objective of our invention to provide processes for the separation of high purity ortho or para-nitrotoluene at high recoveries from a feed mixture comprising the isomer to be separated and at least one other isomer of nitrotoluene, or the separation of a mixture of ortho and para-nitrotoluene from a mixture of all three isomers.

In brief summary, our invention is, in one embodiment, the process for separating para-nitrotoluene from a feed mixture comprising para-nitrotoluene and at least one other isomer of nitrotoluene. The process comprises contacting, at adsorption conditions, the mixture with an adsorbent comprising a type X zeolite containing chromium at the exchangeable cationic sites, or a type Y zeolite containing calcium at the exchangeable cationic sites, selectively adsorbing the para-isomer to the substantial exclusion of the remaining isomers, and thereafter recovering high-purity para-nitrotoluene.

In another embodiment, our invention is a process for separating ortho-nitrotoluene from a feed mixture comprising ortho-nitrotoluene and at least one other isomer of nitrotoluene. The process comprises contacting, at adsorption conditions, the mixture with an adsorbent comprising a type X zeolite containing at the exchangeable cationic sites one or more cations selected from the group consisting of potassium, zinc, nickel, barium, calcium, cobalt, strontium, copper and magnesium, or a type Y zeolite containing at the exchangeable cationic sites one or more cations selected from the group consisting of cesium, potassium, sodium, iron, cobalt, and a combination of the cations potassium and barium, selectively adsorbing the ortho-isomer to the substantial exclusion of the remaining isomers, and thereafter recovering high-purity ortho-nitrotoluene.

In yet another embodiment, our invention is a process for separating a mixture of ortho-nitrotoluene and para-nitrotoluene from a feed mixture comprising ortho, meta and para nitrotoluene. The process comprises contacting, at adsorption conditions, the mixture with an adsorbent comprising a type X zeolite containing at the exchangeable cationic sites one or more cations selected from the group consisting of sodium, nickel, barium, copper, magnesium, calcium, cobalt and strontium, or a type Y zeolite containing at the exchangeable cation sites one or more cations selected from the group consisting of calcium, sodium, iron, cobalt and potassium, and a combination of the cations potassium and barium, selectively adsorbing the ortho and para-isomers to the substantial exclusion of the meta isomer, and thereafter recovering a high-purity mixture of ortho and para-nitrotoluene.

Other objectives and embodiments of our invention encompass details about feed mixtures, adsorbents, desorbent materials and operating conditions, all of which are hereinafter disclosed in the following discussion of each of the facets of the present invention.

DESCRIPTION OF THE INVENTION

The type X and type Y crystalline aluminosilicates or zeolites herein contemplated are described as a three-dimensional network of funadmental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of aromatic hydrocarbon isomers, however, the separation of the isomers apparently occurs because of differences in electrochemical attraction of the different isomers and the adsorbent rather than on pure physical size differences in the isomer molecules.

In hydrated form, the preferred crystalline aluminosilicates generally encompass those zeolites represented by the formula 1 below:

Formula 1

$$M_{2/n}O:Al_2O_3:wSiO_2:yH_2O$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The cations may be any one of a number of cations which will hereinafter be described in detail.

Adsorbents comprising the type X structured and type Y structured zeolites are especially preferred for the adsorptive separation of isomers of this invention. These zeolites are described and defined in U.S. Pat. Nos. 2,882,244 and 3,120,007 respectively. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where "M" represents at least one cation having a valence of not more than 3, "n" represents the valence of "M", and "y" is a value up to about 9 depending upon the identity of "M" and the degree of hydration of the crystal. The cation "M" may be one or more of a number of cations such as the hydrogen cation, the alkali metal cation, or the alkaline earth cations or other selected cations, and is generally referred to as an exchangeable cationic site.

The type Y structured zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where "M" is at least one cation having a valence not more than 3, "n" represents the valence of "M", "w" is a value greater than about 3 up to 8, and "y" is a value up to about 9 depending upon the identity of "M" and the degree of hydration of the crystal.

The term "type X zeolite" and "type Y zeolite" as employed herein shall refer not only to type X structured and type Y structured zeolites containing sodium cations as the cation "M" indicated in the formulas above but also shall refer to those containing other additional cations such as cations included in Groups IA, IIA and the transition metals of the Periodic Table of Elements. Typically both the type X and type Y structured zeolites as initially prepared and as used as a base material for the special adsorbent described herein are predominantly in the sodium form. The term "exchanged cationic site" generally refers to the site in the zeolite occupied by the cation "M". This cation, usually sodium, can be replaced or exchanged with other specific cations, such as those mentioned above, depending on the type of the zeolite to modify characteristics of the zeolite.

The term "base material" as used herein shall refer to a type X or type Y zeolite-containing starting material used to make the special adsorbent described below. Generally the base material will be in the form of particles such as extrudates, aggregates, tablets, pills, macrospheres, or granules produced by grinding any of the above to a desired size range. The type X or type Y zeolite can be present in the base material in concentrations generally ranging from about 75 wt. % to about 98 wt. % of the base material based on a volatile free composition. The remaining material in the base material generally comprises amorphous silica or alumina or both which is present in intimate mixture with the zeolite material. This amorphous material may be an adjunct of the manufacturing process of the type X or type Y zeolite (for example, intentionally incomplete purification of the zeolite during its manufacture) or it may be added to the relatively pure zeolite to aid in forming or agglomerating particles of the zeolite.

One example of a base material is commercially available nominal 1/16 inch extrudate comprising 13X zeolite and a minor amount of amorphous material as binder. This base material is primarily in the sodium form; that is, the cation represented as "M" in Formula 2 above is primarily sodium. By chemical analysis the $Na_2O/Al_2O_3$ ratio of this base material is usually about 0.7 or less and can typically be about 0.6. This, of course, is less than the $0.9\pm0.2$ indicated in Formula 2 above. Other cations such as $H+$ and any of the Group IIA metal cations may be present, primarily as impurities, to supply the remainder of the cations needed for chemical balance and to meet the $0.9\pm0.2$ $Na_2O/Al_2O_3$ ratio. The silica to alumina ratio of this starting material by X-ray determination is about 2.5 and the same ratio by chemical analysis is about 2.6. Normally, the base material, whether in the extrudate or pellet form, is granulated to a particle size range of about 20–40 mesh (Standard U.S. Mesh) before the first ion exchange step is begun. This is approximately the desired particle size of the finished adsorbent.

We have found methods of separating the various isomers of nitrotoluene by use of specific types of zeolites having exchanged therein certain cations as set forth in the following Table:

| Separation Effected | Zeolite Type | Possible Exchange Cation |
|---|---|---|
| Para from mixture of para and at least one other isomer | X | Cr |
| | Y | Ca |
| Ortho from mixture of ortho and at least one other isomer | X | K, Zn, Ni, Ba, Ca, Co, Sr, Cu and Mg |
| | Y | Cs, K, Na, Fe, Co; and K—Ba |
| Ortho and para from mixture of ortho, meta and para | X | Na, Ni, Ba, Cu, Mg, Ca, Co, and Sr |
| | Y | Ca, Na, Fe, Co, K, |

| Separation Effected | Zeolite Type | Possible Exchange Cation |
|---|---|---|
| -continued | | |
| | | and K—Ba |

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

Feed mixtures which can be utilized in the process of this invention will comprise a mixture of at least two isomers of nitrotoluene. Mixtures containing substantial quantities of nitrotoluene may be produced by processes which are well known to the chemical arts. The isomers comprising such mixtures are separated by the adsorbents utilized in the process of this invention according to their configuration depending whether they are of a para-, meta-, or ortho-isomer construction.

To separate the selected isomer from a feed mixture containing the selected isomer and at least one other isomer of nitrotoluene, the mixture is contacted with the appropriate adsorbent comprising a crystalline aluminosilicate and the selected isomer is more selectively adsorbed and retained by the adsorbent while the other isomers are relatively unadsorbed and are removed from the interstitial void spaces between the particles of adsorbent and the surface of the adsorbent. The adsorbent containing the more selectively adsorbed isomer is referred to as a "rich" adsorbent—rich in the more selectively adsorbed isomer.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as raffinate components all of the feed mixture isomers except the selected isomer and the extract stream will contain the selected isomer as the extract component.

Although it is possible by the process of this invention to produce high purity (98% or greater), selected isomers product at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed selected isomer to the concentration of a less selectively adsorbed isomer will be highest in the extract stream, next highest in the feed mixture, and lowest in the raffinate stream. Likewise, the ratio of the less selectively adsorbed isomer to the more selectively adsorbed ortho-isomer will be highest in the raffinate stream, next highest in the feed mixture, and the lowest in the extract stream.

The adsorbent can be contained in one or more chambers where through programmed flow into and out of the chambers separation of the selected isomer is effected. The adsorbent will preferably be contacted with a desorbent material which is capable of displacing the adsorbed selected isomer from the adsorbent. The resultant extract stream comprising the selected isomer and desorbent material is subjected to a separation step so as to obtain high purity selected isomer. Alternatively, the selected isomer could be removed from the adsorbent by purging or by increasing the temperature of the adsorbent or by decreasing the pressure of the chamber or vessel containing the adsorbent or by a combination of these means. The resultant raffinate stream, if it comprises two isomers, may undergo further separation in a manner similar to that which effected separation of the selected isomer, by utilization of an adsorbent which more selectively adsorbs either one of the two isomers.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbed bed systems and are therefore preferred for use in our separation process. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system, it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of our process, it is generally necessary that three separate operational zones be present in order for the process to take place, although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many intances some of the streams can be shut off while others effect an input or output of material. The apparatus which can be utilized to effect the process of this invention can also contain a serieas of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

References can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on Apr. 2, 1969, for further explanation of the simulated moving-bed countercurrent process flow scheme.

Adsorption and desorption conditions for adsorptive separation processes can generally be either in the liquid or vapor phase or both but for aromatic isomer separation processes employing zeolitic adsorbents all liquid-phase operations are usually preferred because of the lower temperature requirements and the slightly improved selectivities associated with the lower temperatures. Preferred adsorption conditions for the process of this invention will include temperatures within the range of from about 70° F. to about 450° F. and will include pressures in the range from about atmospheric to about 500 psig. Pressures higher than about 500 psig. do not appear to effect the selectivity to a measurable amount and additionally would increase the cost of the process. Desorption conditions for the process of the invention shall generally include the same range of temperatures and pressures as described for adsorption operations. The desorption of the selectively adsorbed isomer could also be effected at subatmospheric pressures or elevated temperatures or both or by vacuum purging of the adsorbent to remove the adsorbed isomer but this process is not directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and processes which are generally operated at substantially constant pressures and temperatures to insure liquid phase, the desorbent material relied upon must be judiciously selected to satisfy several criteria. First, the desorbent material must displace the adsorbed feed component from the adsorbent with reasonable mass flow rates without itself being so strongly adsorbed as to unduly prevent the extract component from displacing the desorbent material in a following adsorption cycle. Secondly, desorbent materials must be compatible with the particular adsorbent and the particular feed mixture. More specifically, they must not reduce or destroy the critical selectivity of the adsorbent for the extract component with respect to the raffinate components.

Desorbent materials to be used in the process of this invention should additionally be substances which are easily separable from the feed mixture that is passed into the process. In desorbing the preferentially adsorbed component of the feed, both desorbent material and the extract component are removed in admixture from the adsorbent. Without a method of separation such as distillation of these two materials, the purity of the extract component of the feed stock would not be very high since it would be diluted with desorbent. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture. Preferred desorbent material for use in the process of this invention may be one or a mixture of the compounds toluene and 1-hexanol.

The adsorbents used in the process of our invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

A static test procedure and apparatus may be employed to test various adsorbents with a particular feed mixture to determine the relative retention by the adsorbent of each component of the mixture. The procedure involves mixing together equal quantities of each component, the relative retention of which is to be determined, and a convenient solvent or desorbent material. The resulting solution is then placed in a vessel with a quantity of the appropriate adsorbent and is allowed to remain, with occasional stirring, for about 24 hours. The solution is then analyzed for each component and the relative retention thereof is determined in terms of the percent change (positive or negative) of the concentration of each such component, the relative retention for each component being inversely proportional to the magnitude of the percent change for that component, e.g. the more negative the change in the percentage of a given component, the more strongly that component is adsorbed relative to the other component. A specific adsorbent would clearly be effective in separating a specific isomer when the relative retention for that isomer is negative while the relative retention for the other two isomers is positive. However, one skilled in interpreting static test results and skilled in the art of solid bed separation processes could ascertain from such results that in a dynamic separation scheme where the flow rates of the various streams such as feed and desorbent are controlled variables, a specific adsorbent might be useful in separating a given isomer even when that isomer is one of two isomers in a mixture of the three, both of which exhibit a negative relative retention in the static test, or in in separating two isomers from a mixture of the three even when one of the two isomers has a positive relative retention.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed paraffinic tracer (n-$C_{14}$) and isomers of nitrotoluene, all diluted in desorbent, is injected for a duration of several minutes. Desorbent flow is resumed, and the tracer and the isomers are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

Selectivity, (B), with regard to two given components, is equal to the quotient obtained by dividing the respective retention volumes of such components. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields, or all of these, but in the adsorptive separation of aromatic hydrocarbon isomers with a zeolite-containing adsorbent this is generally not a problem.

To further evaluate promising adsorbent systems and to translate this type of data into a practical isomer separation process requires actual testing of the best system in a continuous countercurrent liquid-solid contacting device. The general operating principles of such a device have been previously described and are found in Broughton U.S. Pat. No. 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback presented at the American Chemical Society, Los Angeles, California, Mar. 28–Apr. 2, 1971.

The example shown below is intended to further illustrate the process of this invention and is not to be construed as unduly limiting the scope and spirit of said process. The example presents static test results for various adsorbents.

EXAMPLE

In this example eighteen adsorbents were tested by the static test procedure previously described to illustrate the retention orders of the three isomers of nitrotoluene for each adsorbent. Each adsorbent used was dried at 500° C. for one hour and then stored in air-tight containers to keep out moisture. For each test one gram of a dried adsorbent was placed in a vial and then two ml of the nitrotoluene test solution were added. The nitrotoluene test solution was prepared by dissolving the three nitrotoluene isomers, each 10% by weight, in toluene. This is about six times the capacity of one gram of adsorbent. The vial was then capped and shaken periodically. After 24 hours, an aliquot of the supernatant solution was analyzed by quantitative GC for each of the three isomers. The selectivity of a given adsorbent was determined by calculating the changes in the isomer distribution relative to the distribution in the test solution. The results are tabulated as follows:

| Adsorbent | Retention Order | Change % | | |
|---|---|---|---|---|
| | | Ortho | Meta | Para |
| Cr—X | P > M > O | +0.4 | +0.1 | −0.5 |
| Cs—Y | O > M > P | −2.0 | +0.1 | +1.9 |
| K—X | O > M > P | −2.9 | +1.2 | +1.7 |
| Zn—X | O > M > P | −3.4 | +1.3 | +2.1 |
| Ca—Y | P > O > M | −1.3 | +2.9 | −1.6 |
| Na—X | O ~ P > M | −0.5 | +1.0 | −0.5 |
| Ni—X | O > P > M | −1.4 | +1.1 | +0.3 |
| Na—Y | O > P > M | −1.7 | +2.5 | −0.8 |
| Ba—X | O > P > M | −1.9 | +1.1 | +0.8 |
| Fe—Y | O > P > M | −1.9 | +2.9 | −1.0 |
| K,Ba—Y | O > P > M | −2.8 | +1.7 | +1.1 |
| Cu—X | O > P > M | −2.8 | +1.7 | +1.1 |
| Co—Y | O > P > M | −2.8 | +4.0 | −1.2 |
| Mg—X | O > P > M | −3.8 | +2.2 | +1.6 |
| Ca—X | O > P > M | −3.9 | +2.4 | +2.0 |
| K—Y | O > P > M | −4.2 | +2.4 | +1.8 |
| Co—X | O > P > M | −4.4 | +2.4 | +2.0 |
| Sr—X | O > P > M | −4.4 | +2.8 | +1.6 |

In view of the above, it is readily apparent solely from the standpoint of which isomers have negative relative retentions that the Cr-X adsorbent would be suitable for separating para from ortho and meta; the Cs-Y, K-X, Zn-X, Ni-X, Ba-X, K-Ba-Y, Cu-X, Mg-X, Ca-X, K-Y, Co-X and Sr-X adsorbents would be suitable for separating ortho from meta and para; and the Ca-Y, Na-X, Na-Y, Fe-Y and Co-Y adsorbents would be suitable for separating a mixture of para and ortho from the meta. It can also be ascertained, however, as discussed before and notwithstanding whether a given isomer has a positive or negative relative retention, that in a dynamic separation scheme a Ca-Y zeolite could be used in separating the para isomer, Na-Y, Fe-Y or Co-Y to separate the ortho isomer; and Ni-X, Ba-X, Cu-X, Mg-X, Ca-X, Co-X, Sr-X, K-Y or K-Ba-Y to separate a mixture of the ortho and para isomers.

We claim as our invention:

1. A process for separating para-nitrotoluene from a feed mixture comprising para-nitrotoluene and at least one other isomer of nitrotoluene, which process comprises contacting at adsorption conditions said mixture with an adsorbent comprising a type X zeolite containing chromium at the exchangeable cationic sites, or a type Y zeolite containing calcium at the exchangeable cationic sites, selectively adsorbing said para isomer to the substantial exclusion of the remaining isomers, and thereafter recovering high-purity para-nitrotoluene.

2. The process of claim 1 further characterized in that said feed mixture contains para-nitrotoluene, meta-nitrotoluene, and ortho-nitrotoluene.

3. The process of claim 1 including the step of treating the adsorbent containing said para-nitrotoluene with a desorbent material to remove said para-nitrotoluene therefrom as a fluid extract stream.

4. The process of claim 3 further characterized in that said desorbent material has an average boiling point substantially different from that of the feed mixture.

5. The process of claim 4 further characterized in that said desorbent material comprises one of the compounds or a mixture of the compounds toluene or 1-hexanol.

6. The process of claim 1 further characterized in that said adsorption conditions include a temperature within the range of from about 70° F. to about 450° F. and at a pressure within the range of from about atmospheric to about 500 psig.

7. The process of claim 6 further characterized in being effected in the liquid phase.

8. A process for separating ortho-nitrotoluene from a feed mixture comprising ortho-nitrotoluene and at least one other isomer of nitrotoluene, which process comprises contacting at adsorption conditions said mixture with an adsorbent comprising a type X zeolite containing at the exchangeable cationic sites one cation selected from the group consisting of potassium, zinc, nickel, barium, calcium, cobalt, strontium, copper and magnesium, or a type Y zeolite containing at the exchangeable cationic sites one cation selected from the group consisting of cesium, potassium, sodium, iron, cobalt, or a combination of the cations potassium and barium, selectively adsorbing said ortho-isomer to the substantial exclusion of the remaining isomers, and thereafter recovering high-purity ortho-nitrotoluene.

9. The process of claim 8 further characterized in that said feed mixture contains para-nitrotoluene, meta-nitrotoluene, and ortho-nitrotoluene.

10. The process of claim 8 including the step of treating the adsorbent containing said orth-nitrotoluene with a desorbent material to remove said ortho-nitrotoluene therefrom as a fluid extract stream.

11. The process of claim 10 further characterized in that said desorbent material has an average boiling point substantially different from that of the feed mixture.

12. The process of claim 11 further characterized in that said desorbent material comprises one of the compounds or a mixture of the compounds toluene or 1-hexanol.

13. The process of claim 8 further characterized in that said adsorption conditions include a temperature within the range of from about 70° F., to about 450° F. and at a pressure within the range of from about atmospheric to about 500 psig.

14. The process of claim 13 further characterized in being effected in the liquid phase.

15. A process for separating a mixture of ortho-nitrotoluene and para-nitrotoluene from a feed mixture comprising ortho, meta and para-nitrotoluene, which process comprises contacting at adsorption conditions said mixture with an adsorbent comprising a type X zeolite containing at the exchangeable cationic sites one cation selected from the group consisting of sodium, nickel, barium, copper, magnesium, calcium, cobalt and strontium, or a type Y zeolite containing at the exchangeable cationic sites one cation selected from the group consisting of calcium, sodium, iron, cobalt and potassium, or a combination of the cations potassium and barium, selectively adsorbing said ortho and para-isomers to the substantial exclusion of said meta isomer, and thereafter recovering a high-purity mixture of ortho and para-nitrotoluene.

16. The process of claim 15 including the step of treating the adsorbent containing said ortho and para-nitrotoluene with a desorbent material to remove said ortho and para-nitrotoluene therefrom as a fluid extract stream.

17. The process of claim 16 further characterized in that said desorbent material has an average boiling point substantially different from that of the feed mixture.

18. The process of claim 17 further characterized in that said desorbent material comprises one of the compounds or a mixture of the compounds toluene or 1-hexanol.

19. The process of claim 15 further characterized in that said adsorption conditions include a temperature within the range of from about 70° F. to about 450° F. and at a pressure within the range of from about atmospheric to about 500 psig.

20. The process of claim 19 further characterized in being effected in the liquid phase.

* * * * *